(12) United States Patent
Sinha (10) Patent No.: US 7,038,027 B2
(45) Date of Patent: May 2, 2006

(54) METHOD OF PREVENTING MODIFICATION OF SYNTHETIC OLIGONUCLEOTIDES

(75) Inventor: Nanda D. Sinha, Boxboro, MA (US)

(73) Assignee: Avecia Biotechnology, Inc., Milford, MA (US)

( * ) Notice: Subject to any disclaimer, the term of this patent is extended or adjusted under 35 U.S.C. 154(b) by 544 days.

(21) Appl. No.: 09/879,859

(22) Filed: Jun. 12, 2001

(65) Prior Publication Data

US 2002/0072593 A1 Jun. 13, 2002

Related U.S. Application Data

(60) Provisional application No. 60/210,757, filed on Jun. 12, 2000.

(51) Int. Cl.
*C07H 19/00* (2006.01)
*C07H 21/00* (2006.01)
*C07H 21/02* (2006.01)
*C07H 21/04* (2006.01)

(52) U.S. Cl. .................... 536/23.1; 536/25.3; 536/26.6
(58) Field of Classification Search ............... 536/23.1, 536/25.3, 26.6
See application file for complete search history.

(56) References Cited

U.S. PATENT DOCUMENTS

| | | | |
|---|---|---|---|
| 4,419,509 A | 12/1983 | Hsiung | 536/27 |
| 5,518,651 A | 5/1996 | Reddy et al. | 252/193 |
| 5,623,068 A | 4/1997 | Reddy et al. | 536/25.34 |
| 5,705,621 A | 1/1998 | Ravikumar | 536/23.1 |
| 5,750,672 A | 5/1998 | Kempe | 536/25.31 |
| 5,760,209 A | 6/1998 | Cheruvallath et al. | 536/25.34 |
| 5,783,690 A | 7/1998 | Cheruvallath et al. | 536/55.3 |
| 5,847,106 A | 12/1998 | Ravikumar et al. | 536/25.34 |
| 5,859,232 A | 1/1999 | Ravikumar | 536/25.3 |
| 6,465,628 B1 * | 10/2002 | Ravikumar et al. | 536/23.1 |

OTHER PUBLICATIONS

Sinha, N.D., et al., "Polymer support oligonucleotide synthesis XVIII[1,2]: use of β-cyanoethyl-N, N-dialkylamino-/N-morpholino phosphoramidite of deoxynucleosides for the synthesis of DNA fragments simplifying deprotection and isolation of the final product," *Nucleic Acids Research*, 12(11) :4539-4557 (1984).

Eritja, R., et al., "A Synthetic Procedure for the Preparation of Oligonucleotides Without Using Ammonia and its Application for the Synthesis of the Oligonucleotides Containing O-4-AlkylThymidines," *Tetrahedron*, 48(20) : 4171-4182 (1992).

Reese, C.B., et al., "Avoidance of sulfur loss during ammonia treatment of oligonucleotide phosphorothioates," Nucleic Acids Research, 25(14): 2943-2944 (1997).

Hsiung, H., et al., "Further improvements on the phosphotriester synthesis of deoxyribooligonucleotides and the oligonucleotide directed site-specific mutagenesis of *E. coli* lipoprotein gene," *Nucleic Acids Research*, 11(10) :3227-3239 (1983).

* cited by examiner

*Primary Examiner*—Jezia Riley
(74) *Attorney, Agent, or Firm*—Hamilton, Brook, Smith & Reynolds, P.C.

(57) ABSTRACT

The present invention relates to a method of preventing modification of a synthetic oligonucleotide or oligonucleotide analog during removal of at least one β-cyanoethyl protecting group from the oligonucleotide or oligonucleotide analog. The method involves contacting the oligonucleotide or oligonucleotide analog with a basic solution having at least one acrylonitrile scavenger, such as t-butylamine, at a sufficient temperature and for a sufficient period of time to remove at least one β-cyanoethyl protecting group. The present invention also relates to a method of producing a synthetic oligonucleotide or oligonucleotide analog.

78 Claims, 6 Drawing Sheets

METHOD OF PREVENTING MODIFICATION OF SYNTHETIC OLIGONUCLEOTIDES

RELATED APPLICATION

This Application claims the benefit of U.S. Provisional Application No. 60/210,757 filed Jun. 12, 2000, the entire teachings of which are incorporated herein by reference.

BACKGROUND OF THE INVENTION

Oligonucleotides are synthesized routinely on solid supports using β-cyanoethyl phosphoramidite chemistry on a large scale for antisense therapeutics or on a small scale for diagnostic/molecular biology purposes. This chemistry was developed using silica based CPG beads as solid supports to facilitate deprotection and purification. Subsequently, this chemistry was adapted to synthesize oligonucleotides using rigid polystyrene based supports. In addition, large scale synthesis of oligonucleotides for use in antisense and related therapies has become increasingly important since FDA approval of a oligonucleotide analog for the treatment of CMV. Several other oligonucleotide analog are currently in clinical trials. Presently, kilogram quantities of oligonucleotides with either phosphate diester or phosphorothioated diester linkages are being synthesized using β-cyanoethyl phosphoramidite chemistry for clinical trials and other applications.

For pharmaceutical applications, the desired oligonucleotide must be separated from substantially all impurities generated during synthesis. Impurities are generally removed by reverse phase high pressure liquid chromatography (HPLC) and/or ion-exchange chromatography. However, those impurities which are structurally similar to the desired product are difficult to remove because their structural similarity to the desired product causes them to have a similar chromatographic mobility. Therefore, it is desirable to improve synthetic methodology so that impurities which have a similar structure to the desired product are not produced.

SUMMARY OF THE INVENTION

The present invention relates to the discovery that acrylonitrile, which is released during cleavage of a β-cyanoethyl phosphate protecting group from a synthetic oligonucleotide or oligonucleotide analog, can react with a nucleophilic group on the oligonucleotide or oligonucleotide analog to generate an impurity which is structurally similar to the desired oligonucleotide or oligonucleotide analog.

The method of the present invention substantially prevents modification of a synthetic oligonucleotide or oligonucleotide analog during cleavage of at least one β-cyanoethyl protecting group from the oligonucleotide or oligonucleotide analog. The method involves contacting a β-cyanoethyl protected oligonucleotide or oligonucleotide analog with a solution of an acrylonitrile scavenger in an organic solvent under conditions sufficient (e.g., at a sufficient temperature and for a sufficient period of time) to remove at least one β-cyanoethyl protecting group. t-Butylamine is a preferred acrylonitrile scavenger. Suitable organic solvents include nucleophilic solvents such as pyridine, ethers such as tetrahydrofuran or dioxane, nitriles such as acetonitrile, haloalkanes such as methylene chloride, esters such as ethyl acetate, methyl propionate and ethyl propionate, alcohols such as ethanol or methanol, and dimethyl formamide. One group of preferred solvents include haloalkanes, esters, alcohols and dimethyl formamide. Another group of preferred solvents include pyridine and acetonitrile.

In another embodiment, the method involves contacting a β-cyanoethyl protected oligonucleotide or oligonucleotide analog with an aqueous basic solution having at least one acrylonitrile scavenger, such as t-butylamine. The basic solution is preferably an aqueous ammonium hydroxide solution. The oligonucleotide or oligonucleotide analog is contacted with the aqueous basic solution having at least one acrylonitrile scavenger under conditions sufficient to remove at least one β-cyanoethyl protecting group from the oligonucleotide or oligonucleotide analog.

In another embodiment, the β-cyanoethyl protected oligonucleotide or oligonucleotide analog is contacted with a solution containing an organic solvent and at least one acrylonitrile scavenger prior to being contacted with an aqueous basic solution containing an acrylonitrile scavenger.

In addition, at least one nucleobase protecting group can be removed when the β-cyanoethyl protected oligonucleotide or oligonucleotide analog is contacted with either the organic or the aqueous basic solution containing the acrylonitrile scavenger. In addition, the oligonucleotide or oligonucleotide analog can be cleaved concurrently from a solid support by contact with either the organic or the aqueous basic solution containing the acrylonitrile scavenger.

The present invention also relates to a method of producing an oligonucleotide or oligonucleotide analog in which modification of the oligonucleotide or oligonucleotide analog is substantially prevented. In the method of producing an oligonucleotide or oligonucleotide analog, the oligonucleotide or oligonucleotide analog having at least one β-cyanoethyl protecting group is synthesized, typically using phosphoramidite chemistry. The synthesized β-cyanoethyl protected oligonucleotide or oligonucleotide analog is then contacted with a solution of at least one acrylonitrile scavenger in an organic solvent for a sufficient period of time at a sufficient temperature to remove at least one β-cyanoethyl protecting group. In an alternative embodiment, the synthesized β-cyanoethyl protected oligonucleotide or oligonucleotide analog is contacted with an aqueous basic solution having at least one acrylonitrile scavenger for a sufficient period of time at a sufficient temperature to remove at least one β-cyanoethyl protecting group. In another embodiment, the synthesized β-cyanoethyl protected oligonucleotide or oligonucleotide analog is first contacted with a solution of at least one acrylonitrile scavenger in an organic solvent and then subsequently contacted with an aqueous basic solution having at least one acrylonitrile scavenger for a sufficient period of time at a sufficient temperature to remove at least one β-cyanoethyl protecting group.

Typically, the β-cyanoethyl phosphate protecting groups are cleaved from a synthetic oligonucleotides or oligonucleotide analogs by treating the synthetic oligonucleotide or oligonucleotide analog with an aqueous ammonium hydroxide solution. A chromatogram of the crude product after ammonium hydroxide treatment generally reveals additional peaks, other than desired oligonucleotide or oligonucleotide analog. These anomalies are predominantly found with sequences rich in thymine or guanine bases or in oligonucleotides which have been modified so that they contain an aliphatic amine group. As described herein, a MALDITOF mass spectrum of the crude oligonucleotide or oligonucleotide analog product after treatment with ammonium hydroxide indicated that the primary impurity has a mass of 52–54 unit more than the desired mass of oligonucleotide or oligonucleotide analog indicating that it was derived from modification of the desired oligonucleotide with acrylonitrile, a by-product from cleavage of the β-cyanoethyl protecting group.

Without wishing to be bound by any theory, it is believed that the method of the invention has the advantage of removing acrylonitrile produced during removal of the β-cyanoethyl protecting groups from the aqueous basic solution by reacting the acrylonitrile with an acrylonitrile scavenger. This reduces the amount of impurities generated during cleavage and deprotection that are structurally similar to the desired oligonucleotide product, such as oligonucleotides and oligonucleotide analogs in which one or more nucleobase has reacted with acrylonitrile. Therefore, the purification of the desired product is more facile resulting in a higher recovery of the purified product.

BRIEF DESCRIPTION OF THE DRAWINGS

FIGS. 1A, 1B and 1C are ion exchange HPLC chromatograms as described below. The column type was DNA PAC PA-100 (column s/n: 1305). Eluent A was 25 mM Tris pH 8. Eluent B was 25 mM Tris, 375 mM NaClO4 pH 8. The System Name was IEX2. Channel Description was 260 nm. Gradient was 10 to 60%B IN 40 min at a flowrate of 1.5 m/min and temperature of 45 C.

FIG. 2A is a MALDITOF mass spectrum of the phosphate diester oligonucleotide in FIG. 1A. PSI NH4OH TIPPED. Method was DNA1. Mode was linear. The Accelerating Voltage was 25000. The Grid Voltage was 92.500%. The Guide Wire Voltage was 0.150%. Scans Averaged were 156. Pressure at 3.09e-07. Laser at 2620. Negative Ions was OFF. Low Mass Gate was 500.0. Delay was 250 ON.

FIG. 2B is a MALDITOF mass spectrum of the phosphate diester oligonucleotide in FIG. 1B. PSI NH4OH+10% t-Butylamine method was DNA1. Mode was Linear. Accelerating Voltage was 25000. Grid Voltage was 92.500%. Guide Wire Voltage was 0.150%. Scans Averaged were 54. Pressure was 3.05e-07. Laser at 2620. Negative Ions was OFF. Low Mass Gate was 500.0. Delay was 250 ON.

FIG. 2C is a MALDITOF mass spectrum of the phosphate diester oligonucleotide in FIG. 1C. PSI NH4OH+DDT TIPPED. Method was DNA1. Mode was Linear. Accelerating Voltage was 25000. Grid Voltage was 92.500%. Guide Wire Voltage was 0.150%. Scans Averaged were 54. Pressure was 3.05e-07. Laser at 2620. Negative Ions was OFF. Low Mass Gate was 500.0. Delay was 250 ON.

DETAILED DESCRIPTION OF THE INVENTION

The present invention relates to the discovery that modification of a synthetic oligonucleotide or oligonucleotide analog with acrylonitrile generated during the cleavage of β-cyanoethyl phosphate protecting groups can be ameliorated or substantially prevented by addition of an acrylonitrile scavenger to an aqueous basic solution used to cleave the β-cyanoethyl protecting group. Alternatively, modification of a synthetic oligonucleotide or oligonucleotide analog by acrylonitrile can be prevented by treating a β-cyanoethyl protected oligonucleotide or oligonucleotide analog with an acrylonitrile scavenger in an organic solvent.

A β-cyanoethyl protecting group is typically used to protect an oxygen or sulfur attached to the phosphorous backbone of an oligonucleotide or a oligonucleotide analog during synthesis. A β-cyanoethyl protecting group can be represented by the following structural formula:

β-cyanoethyl protecting groups can be removed by treatment with an basic solution. For details on conditions for the removal of β-cyanoethyl protecting groups see Sinha, et al., *Nucleic Acids Research* (1984), 12(11):4539 and Sinha, U.S. Pat. No. 4,725,677, the entire teachings of which are incorporated herein by reference.

The term "aqueous basic solution," as used herein, refers to an aqueous solution or an aqueous solution which contains a water miscible organic solvent, such as an alcohol, tetrahydrofuran, acetonitrile, and dimethyl formamide. When an organic solvent is present in the aqueous solution, it typically is present at a concentration of less than 50%. The base is typically ammonia, a substituted or unsubstituted aliphatic amine, a substituted or unsubstituted aromatic amine, an alkaline metal hydroxide or an alkaline earth metal hydroxide. Aqueous ammonium hydroxide is a preferred basic solution. In a preferred embodiment, nucleobase protecting groups are also removed by treatment with the aqueous basic solution having at least one acrylonitrile scavenger.

When the β-cyanoethyl protecting group is removed by treatment with a base, such as ammonium hydroxide, acrylonitrile is formed (e.g., see Scheme I).

Scheme I: Deprotection of a β-cyanoethyl protecting group.

In Scheme I, $X^1$ and $X^2$ are each, independently, an oxygen or a sulfur. The acrylonitrile formed during removal of the β-cyanoethyl protecting group is a Michael acceptor and, therefore, can react with exo- or endocyclic nucleophilic groups on the oligonucleotide or oligonucleotide analog under basic reaction conditions. For example, the acrylonitrile can react with a thymidine base by adding to $N^3$ as shown in Scheme II.

Scheme II:
Cyanoethylation of a nucleobase during ammonium hydroxide treatment.

In the method of the invention, cyanoethylation of the synthetic oligonucleotide or oligonucleotide analog is ameliorated or substantially prevented by removing the β-cyanoethyl protecting groups with a solution that has at least one acrylonitrile scavenger. Modification of an oligonucleotide or oligonucleotide analog with acrylonitrile during treatment to remove at least one β-cyanoethyl protecting group is substantially prevented if after treatment to remove at least one β-cyanoethyl protecting group no impurity exists that has a molecular weight 52–53 mass units higher than the desired oligonucleotide or oligonucleotide analog, or the detectible amount of such impurity is less than 0.5% when compared to the desired oligonucleotide or oligonucleotide analog.

An acrylonitrile scavenger is a compound that can react with acrylonitrile rendering it unreactive to nucleophilic groups of the oligonucleotide or oligonucleotide analog, such as those of the nucleobases. Preferably, the acrylonitrile scavenger can also cleave β-cyanoethyl protecting groups of a β-cyanoethyl protected oligonucleotide or oligonucleotide analog to generate the desired backbone of the oligonuclotide or oligonucleotide analog (e.g., phosphodiester, phosphorothioate, methyl phosphonate, ect.). Acrylonitrile scavengers are preferably hindered to avoid reaction with the nucleobases. For example, unhindered primary amines can react with cytosine and adenosine by displacing the $N^4$-amine of cytosine and the $N^6$-amine of adenosine (Hsiung, et al., *Nucleic Acid Research* (1983), 11(10):3227). Therefore, acrylonitrile scavengers which are primary aliphatic amines or primary aliphatic thiols should be sterically hindered. A sterically hindered thiol or sterically hindered primary aliphatic amine is a thiol or amine group bound to an aliphatic secondary or tertiary carbon atom or a primary carbon provided that the primary carbon is attached to a secondary or tertiary carbon atom or an aromatic or heteroaromatic group. Acrylonitrile scavengers that may be employed include substituted or unsubstituted aliphatic hydroxyl compounds. Preferred acrylonitrile scavengers are substituted or unsubstituted sterically hindered aliphatic thiol, a substituted or unsubstituted aromatic thiol, a substituted or unsubstituted aromatic hydroxyl (e.g., phenol), a substituted or unsubstituted secondary aliphatic amine, a substituted or unsubstituted sterically hindered primary aliphatic amine, or a substituted or unsubstituted primary or secondary aromatic amine. More preferably, the acrylonitrile scavenger is t-butylamine.

Since acrylonitrile scavengers preferably cleave β-cyanoethyl protecting groups, modification of a synthetic oligonucleotide or oligonucleotide analog can be substantially prevented by treating a β-cyanoethyl protected oligonucleotide or oligonucleotide analog with an organic solvent containing an acrylonitrile scavenger for sufficient time, preferably about 0.5 h to about 2 h, and at sufficient temperature, preferably about 15° C. to about 30° C., to remove at least one β-cyanoethyl group. The acrylonitrile scavenger is often present in the organic solvent at a concentration of about 0.5% (vol/vol) to about 50% (vol/vol), preferably at about 3% (vol/vol) to about 25% (vol/vol), more preferably at about 1% (vol/vol) to about 15% (vol/vol).

In another embodiment, a synthetic oligonucleotide or oligonucleotide analog having at least one β-cyanoethyl protecting group is contacted with an aqueous basic solution containing at least one acrylonitrile scavenger for sufficient time and at sufficient temperature to remove at least one β-cyanoethyl group. The acrylonitrile scavenger is often present in the basic solution at a concentration of about 0.5% (vol/vol) to about 50% (vol/vol), preferably at about 3% (vol/vol) to about 25% (vol/vol), more preferably at about 1% (vol/vol) to about 15% (vol/vol).

When the amine groups of the nucleobases of the oligonucleotide or oligonucleotide analog are protected with a base labile protecting group, such as by formation of an amide protecting group, the protecting groups can be removed when oligonucleotide or oligonucleotide analog is contacted with the aqueous basic solution containing at least one acrylonitrile scavenger. In addition, if the oligonucleotide is attached to a solid support by a base labile linker, such as a succinamide linker or an oxamide linker, it can be cleaved from the solid support by contact with the apueous basic solution containing at least one acrylonitrile scavenger. Similarly, nucleobase protecting groups can be removed and the oligonucleotide can be cleaved from the solid support when oligonucleotide or oligonucleotide analog is contacted with an organic solution containing at least one acrylonitrile scavenger if the acrylonitrile scavenge is an amine such as a substituted or unsubstituted secondary aliphatic amine or a substituted or unsubstituted sterically hindered primary aliphatic amine.

In the method of the invention, the oligonucleotide or oligonucleotide analog is typically contacted with the aqueous basic solution containing the acrylonitrile scavenger for up to about 48 hrs. Typically, the aqueous basic solution is at a temperature of about 20° C. to about 100° C. The length of time which the oligonucleotide or oligonucleotide analog is contacted with the aqueous basic solution containing the acrylonitrile scavenger, and the temperature of the solution depends on whether there are nucleobase protecting groups to remove and the type of nucleobase protecting groups used. For example, when the amine groups of adenine and cytosine are protected with benzoyl protecting groups, and the amine group of guanine is protected with an isobutyryl protecting group, a sufficient time and temperature for contact of the oligonucleotide with the aqueous basic solution containing the acrylonitrile scavenger is about 6 hrs. to about 16 hrs. at about 45° C. to about 65° C., preferably at 55° C. However, when fast deprotecting groups are used (phenoxyacetyl for the amine groups of adenine and guanine, and isobutyryl for the amine group of cytosine), about 2 hrs. to about 4 hrs. at about room temperature is a sufficient. If there are no nucleobase protecting groups to be removed, about 0.5 hrs. to about 2 hrs. at 20° C. to 35° C., preferably at 25° C. is generally a sufficient to remove the β-cyanoethyl protecting groups and, in certain advantageous embodiments, to remove the oligonucleotide or oligonucleotide analog from the solid support.

As discussed above, a β-cyanoethyl protected oligonucleotide or oligonucleotide analog can be treated with a solution of an acrylonitrile scavenger in an organic solvent to remove β-cyanoethyl protecting groups and, when the acrylonitrile scavenger is a secondary aliphatic amine or a sterically hindered primary aliphatic amine such as t-butylamine, to remove nucleobase protecting groups from the oligonucleotide or oligonucleotide analog and cleave the oligonucleotide or oligonucleotide analog from the solid support. When an organic solution containing an acrylonitrile scavenger is used to remove nucleobase protecting groups and to cleave the oligonucleotide or oligonucleotide analog from the solid support, the β-cyanoethyl protected oligonucleotide or oligonucleotide analog is contacted with the organic solution which is heated to about 35° C. to about 100° C. for about 6 hrs. to about 48 hrs. Preferably, the oligonucleotide is contacted with the organic solution for about 6 hrs. to about 16 hrs., and the organic solution is preferably heated to about 45° C. to about 65° C.

In another embodiment, the β-cyanoethyl protected oligonucleotide or oligonucleotide analog can be first contacted with an organic solvent containing an acrylonitrile scavenger under the conditions described above for cleavage of β-cyanoethyl groups with an organic solution containing an acrylonitrile scavenger. The oligonucleotide or oligonucleotide analog is then contacted with an aqueous basic solution containing at least one acrylonitrile scavenge under the conditions described above for cleavage of β-cyanoethyl groups using an aqueous basic solution containing an acrylonitrile scavenger.

Nucleobases include naturally occurring bases, such as adenine, guanine, cytosine, thymine, and uracil and modified bases such as 7-deazaguanine, 7-deaza-8-azaguanine, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouracil, 2,6-diaminopurine, 8-aminopurine, 4-triazolo-5-methylthymine, 5-methylcytosine, 5-propyncytosine, 5-propynuracil and 4-triazolo-5-methyluracil.

A protected nucleobase is a nucleobase in which reactive functional groups of the base are protected with nucleobase protecting groups. Typically, nucleobases have amine groups which can be protected with an amine protecting group. Amine protecting groups are known to those skilled in the art. For examples of amine protecting groups see Greene, et al., *Protective Groups in Organic Synthesis* (1991), John Wiley & Sons, Inc., pages 309–405, the teachings of which are incorporated herein by reference in their entirety. Preferably, amines are protected as amides. The amine groups of adenine and cytosine are typically protected with benzoyl protecting groups, and the amine groups of guanine is typically protected with an isobutyryl protecting group. However, other protection schemes may be used. For example, for fast deprotection, the amine groups of adenine and guanine can be protected with phenoxyacetyl groups, and the amine group of cytosine can be protected with an acetyl or isobutyryl group. Conditions for removal of the nucleobase protecting group to generate the original functional group will depend on the protecting group used. When amino groups are protected by the formation of an amide group, it is typically removed by treating the oligonucleotide with a concentrated ammonium hydroxide solution at about 20° C. to about 65° C. for about 2 hrs. to about 48 hrs.

Synthetic oligonucleotides or oligonucleotide analogs are those that are chemically synthesized, and are not extracted from biological materials. The method of the invention is particularly useful for synthetic oligonucleotides and oligonucleotide analogs which are rich in thymine and/or guanine nucleobases, for example, oligonucleotides or oligonucleotide analogs in which at least about 5% of the nucleobases are either thymine or guanine. Preferably, at least about 10% of the nucleobases of the oligonucleotide or oligonucleotide analog are guanine or thymine. More preferably, at least about 25% of the nucleobases are guanine or thymine. Still more preferably, at least about 50% of the nucleobases are guanine or thymine. Most preferably, all of the nucleobases are guanine or thymine.

A solid support for oligonucleotide synthesis is an organic or inorganic polymer that is insoluble in the reagents used for oligonucleotide synthesis. Typically, rigid polystyrene or controlled-pore glass silica is used as a solid support in oligonucleotide synthesis. Additionally, microporous or soft gel supports, especially poly(acrylamide) supports, such as those more commonly employed for the solid phase synthesis of peptides may be employed if desired. Preferred poly(acrylamide) supports are amine-functionalized supports, especially those derived from supports prepared by copolymerization of acryloyl-sarcosine methyl ester, N,N-dimethylacryamide and bis-acryloylethylenediamine, such as the commercially available (Polymer Laboratories) support sold under the catalogue name PL-DMA. The procedure for preparation of the supports has been described by Atherton, E. and Sheppard, R. C. in *Solid Phase Peptide Synthesis: A Practical Approach*, (1984) IRL Press at Oxford University Press, the microporous supports of which are incorporated herein by reference. The functional group on such supports is a methyl ester and this is initially converted to a primary amine functionality by reaction with an alkyl diamine, such as ethylene diamine.

The oligonucleotides employed in or produced by the method of the present invention include phosphate diesters (e.g., deoxyribonucleic acid and ribonucleic acid) or oligonucleotide analogs. A oligonucleotide analog is understood to mean herein a DNA or RNA oligonucleotide molecule that contains chemically modified nucleotides. For example, oligonucleotide analogs can have a modified nucleobase, such as 7-deazaguanine, 7-deaza-8-azaguanine, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouracil, 2,6-diaminopurine, 8-aminopurine, 4-triazolo-5-methylthymine, 5-methylcytosine and 4-triazolo-5-methyluracil. Oligonucleotide analogs can also be modified at the sugar moiety. For example, a hydroxy group of the sugar moiety can be modified through the addition of 2'-O-methyl groups, or the sugar can be L-ribose or L-deoxyribose instead of the naturally occurring D-ribose or D-deoxyribose. Oligonucleotide analogs also include oligonucleotides which are modified at the phosphate backbone. For example, phosphorothioates, methyl phosphates or methyl phosphonates are oligonucleotide analogs. A oligonucleotide analog can have a portion of the oligonucleotide which is a non-nucleic acid molecules such as PNA (see Egholm, et al., *J. Am. Chem. Soc.* (1992), 114:1895) or a morpholino antisense oligomers (see Summerton and Weller, *Antisense and Nucleic Acid Drug Dev.* (1997), 7:187) provided that at least one β-cyanoethyl protecting group is used in the synthesis of the oligonucleotide analog. In addition, an oligonucleotide analog can be an oligonucleotide which has been modified at the 3'- or 5'-end with, for example, a fluorescent dye, such as fluoroscein or rhodamine, a linker, such as an alkyl amine or a protected thiol alkyl linker, an intercalator, such as acridine, a group which increases cellular uptake, such as cholesterin, a hapten, such as dinitrophenol, or a label or reporter group, such as biotin or digoxgenin.

An aliphatic thiol group, an aliphatic hydroxyl group or an aliphatic amine group is a thiol, hydroxyl or amine group covalently bound to a substituted or unsubstituted aliphatic group. A primary aliphatic amine is an amine attached to one aliphatic group (e.g., t-butylamine). A secondary aliphatic amine is an amine attached to two aliphatic groups (e.g., diisopropylamine, morpholine, or piperazine). A sterically hindered primary aliphatic amine or a sterically hindered aliphatic thiol is an amine or a thiol bound to an aliphatic secondary or tertiary carbon atom or a primary carbon provided that the primary carbon is attached to at least a secondary or tertiary carbon atom or an aromatic or heteroaromatic group. t-Butylamine is an example of an amine group attached to an aliphatic tertiary carbon atom. s-Butylamine is an example of an amine group attached to an aliphatic secondary carbon atom. Benzyl mercaptan is an example of a thiol attached to a primary carbon which is also attached to an aromatic group.

Aliphatic groups, as used herein, include straight chained or branched $C_1$–$C_{18}$ hydrocarbons which are completely saturated or which contain one or more unconjugated double bonds, or cyclic $C_3$–$C_8$ hydrocarbons which are completely saturated or which contain one or more unconjugated double bonds provided that at least one carbon bound to a thiol, hydroxyl or amine group is not part of a double bond. Lower alkyl groups are straight chained or branched $C_1$–$C_8$ hydrocarbons or $C_3$–$C_8$ cyclic hydrocarbons which are completely saturated. The aliphatic groups of acrylonitrile scavengers which are sterically hindered aliphatic thiols, aliphatic hydroxyls, secondary aliphatic amines or sterically hindered primary aliphatic amines are preferably a lower alkyl group.

Aliphatic groups can be substituted or unsubstituted. Suitable substituents for aliphatic groups include substituted or unsubstituted aromatic groups, substituted or unsubstituted heteroaromatic groups, substituted or unsubstituted heterocycloalkyl groups, halogenated aromatic groups, halogenated lower alkyl (e.g. trifluoromethyl and trichloromethyl), —O-(aliphatic group or substituted aliphatic group), —O-(aromatic group or substituted aromatic group), halo, cyano, nitro, —S-(aliphatic or substituted aliphatic group), and —S-(aromatic or substituted aromatic).

The term "haloalkanes" as used herein includes straight chained or branched $C_1$–$C_8$ hydrocarbons which are completely saturated and which contain one to 18 halo group. In addition, the term "haloalkanes" includes cyclic $C_3$–$C_8$ hydrocarbons which are completely saturated and which contain one or 16 halo groups. Halo groups include fluoro, chloro, bromo, and iodo groups.

Aromatic groups include carbocyclic ring systems (e.g. phenyl) and fused polycyclic, carbocyclic ring systems (e.g. naphthyl, anthracenyl and 1,2,3,4-tetrahydronaphthyl).

Esters include groups represented by the following formula:

wherein R and $R_1$ are each, independently, an aliphatic group, an aromatic group or an arylalkyl group.

Alcohols include groups represented by the following formula:

$R_2$—OH wherein $R_2$ is an aliphatic group.

Arylalkyl groups, as used herein, include an aromatic substituent that is linked to a moiety by an aliphatic group preferably having from one to about six carbon atoms.

Heteroaromatic groups, as used herein, include heteroaryl ring systems (e.g., thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isoxazoles, isothiazoles, tetrazoles, or oxadiazoles) and heteroaryl ring systems in which a carbocyclic aromatic ring, carbocyclic non-aromatic ring or heteroaryl ring is fused to one or more other heteroaryl rings (e.g., benzo(b)thienyl, benzimidazole, indole, tetrahydroindole, azaindole, indazole, quinoline, imidazopyridine, purine, pyrrolo[2,3-d]pyrimidine, and pyrazolo[3,4-d]pyrimidine).

A heterocycloalkyl group, as used herein, is a non-aromatic ring system that has 5 to 7 atoms and includes at least one heteroatom, such as nitrogen, oxygen, or sulfur. Examples of heterocycloalkyl groups include morpholines, piperidines, and piperazines.

Suitable substituents for aromatic groups, heteroaromatic groups or heterocycloalkyl groups include halo, nitro, cyano, halogenated lower alkyl groups, lower alkyl ethers and lower alkyl thioethers.

Another embodiment of the invention is a method of manufacturing an oligonucleotide or an oligonucleotide analog. The method of manufacture involves the steps of synthesizing an oligonucleotide or an oligonucleotide analog, then contacting the oligonucleotide or oligonucleotide analog with an aqueous basic solution having at least one acrylonitrile scavenger for a sufficient period of time at a sufficient temperature to remove at least one β-cyanoethyl protecting group.

The oligonucleotide can be synthesized by any method for synthesizing oligonucleotides or oligonucleotide analogs known to those skilled in the art, including both solid phase and solution phase methods, provided the oligonucleotide or oligonucleotide analog synthesized has at least one β-cyanoethyl protecting group. Typically oligonucleotides or oligonucleotide analogs are synthesized using phosphoramidite chemistry (see Caruthers, M. H., *Science* (1985), 230:281, the entire teachings of which are incorporated herein by reference). Other methods of synthesizing oligonucleotides or oligonucleotide analogs include the phosphate diester and phosphate triester approach (see Caruthers, M. H., *Acc. Chem. Res.* (1980), 13:155; Itakura, et al., *Ann. Rev. Biochem.* (1984), 53:323; Khorana, et al., *J. Molecular Biology* (1972), 72:209; Khorana, et al., *Cold Spring Harbor Symp. Quant. Biol.* (1966), 31:39, the entire teachings of which are incorporated herein by reference), or H-phosphonate approach (see Andrus, et al., *Tetrahedron Lett.* (1988), 29:861; Froehler, B. C., *Tetrahedron Lett.* (1986a), 27:5565; Froehler, B. C., *Tetrahedron Lett.* (1986b), 27:5575; Gregg, et al., *Tetrahedron Lett.* (1987), 27:4051, the entire teachings of which are incorporated herein by reference). In a preferred embodiment, a portion of the oligonucleotide or oligonucleotide analog can be synthesized by phosphoramidite chemistry and a different portion of the oligonucleotide can be synthesized by another method, such as the phosphate diester approach, the phosphate triester approach or the H-phosphonate approach. In a more preferred embodiment, the oligonucleotide or oligonucleotide analog is synthesized entirely using phosphoramidite chemistry.

EXPERIMENTAL

Example 1

Comparative Deprotection Results

Figure 1A:
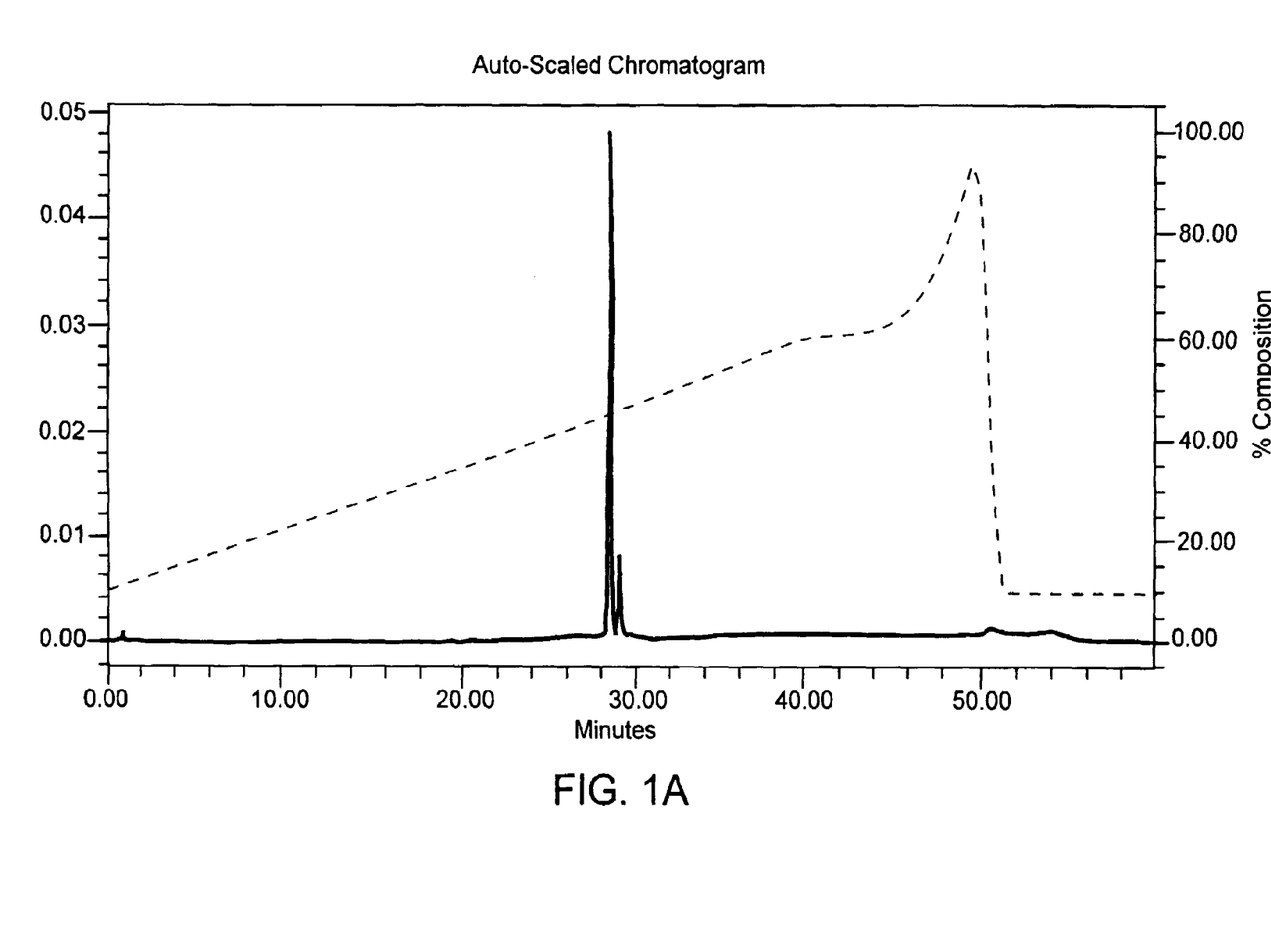
FIG. 1A is an ion exchange HPLC chromatogram of a phosphate diester oligonucleotide having 31 thymine bases which was cleaved from a polystyrene solid support and deprotected by treatment with ammonium hydroxide at 50° C. for 16 hrs.
Figure 1B:
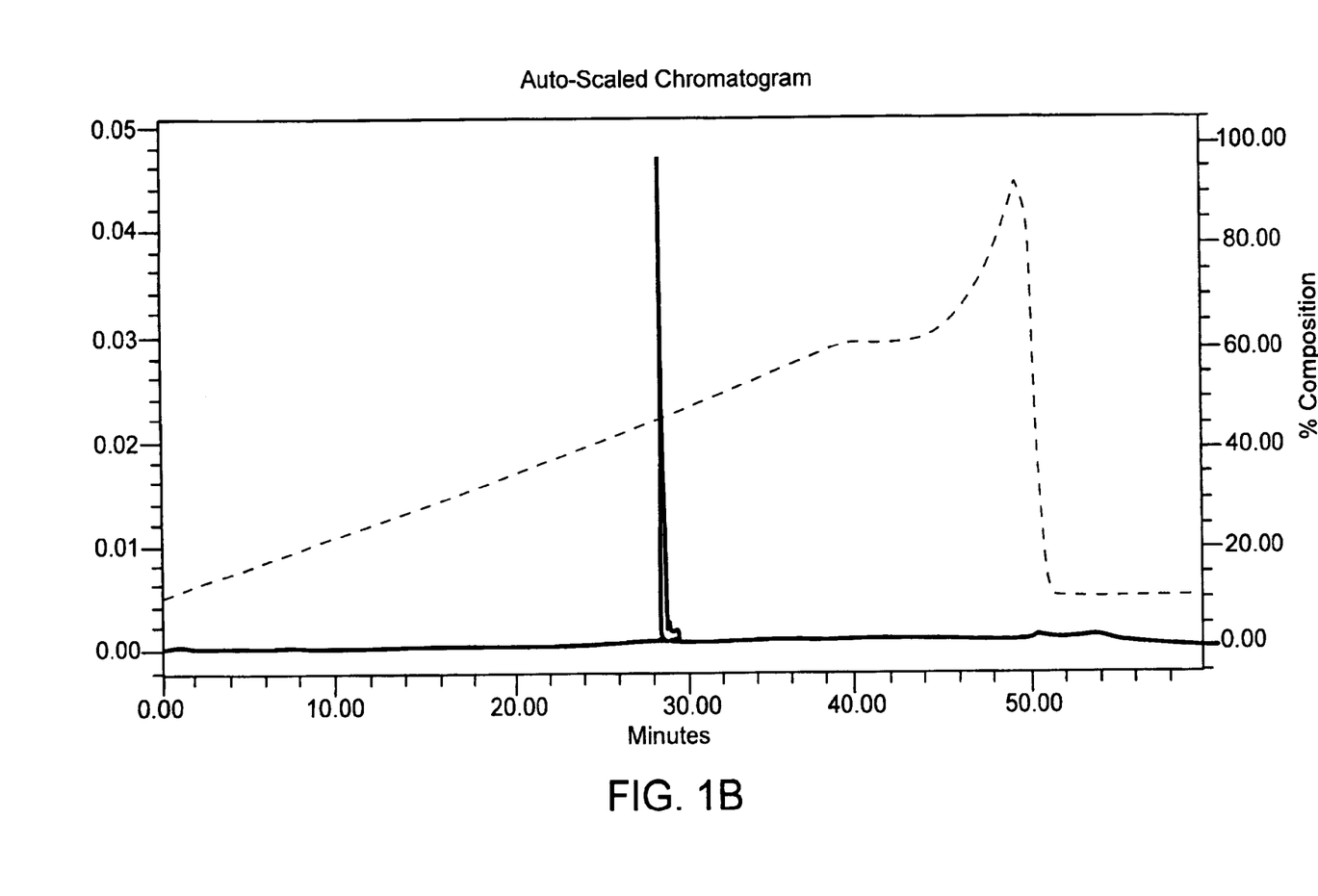
FIG. 1B is an ion exchange HPLC chromatogram of a phosphate diester oligonucleotide from the same synthesis batch as the phosphate diester in FIG. 1A which was cleaved from the solid support and deprotected by treatment with 10% t-butylamine in ammonium hydroxide at 50° C. for 16 hrs.
Figure 1C:
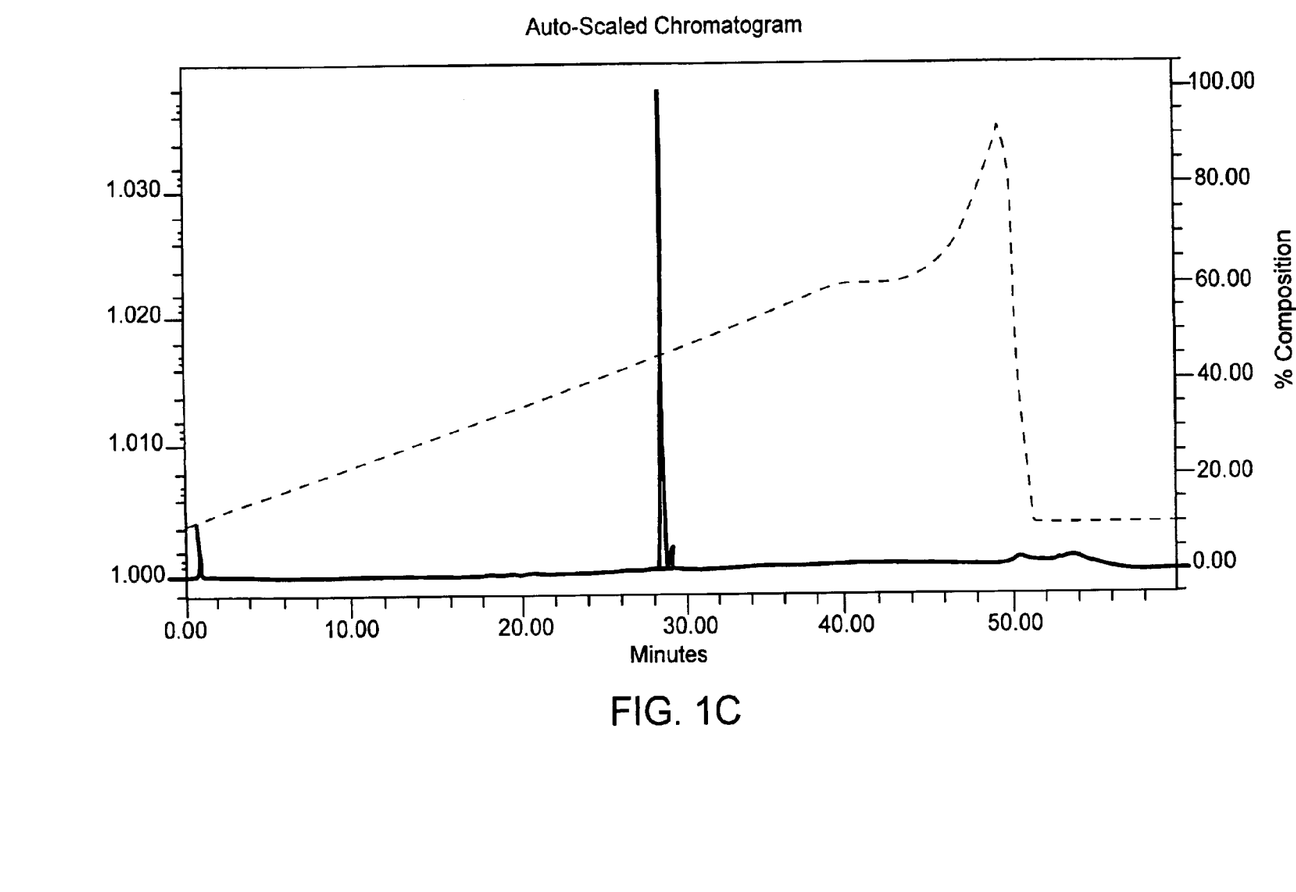
FIG. 1C is an ion exchange HPLC chromatogram of a phosphate diester oligonucleotide from the same synthetic batch as the phosphate diester in FIG. 1A which was cleaved from the solid support and deprotected by treatment with 5% DTT in ammonium hydroxide at 50° C. for 16 hrs.
Figure 2A:
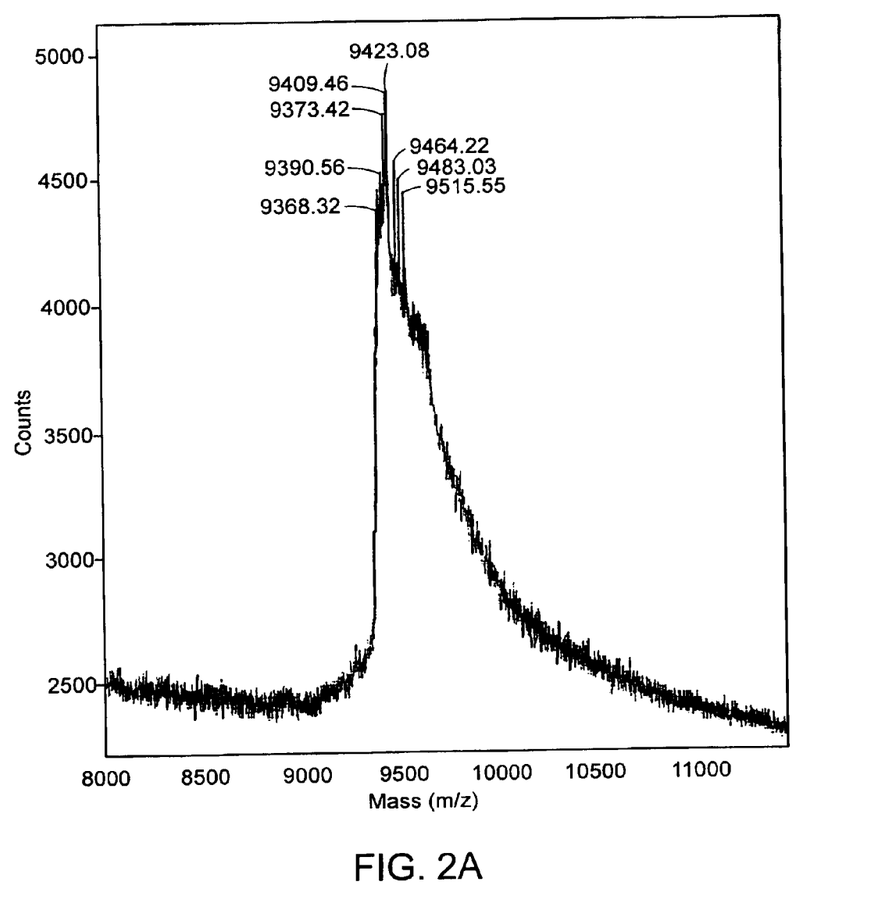
Figure 2B:
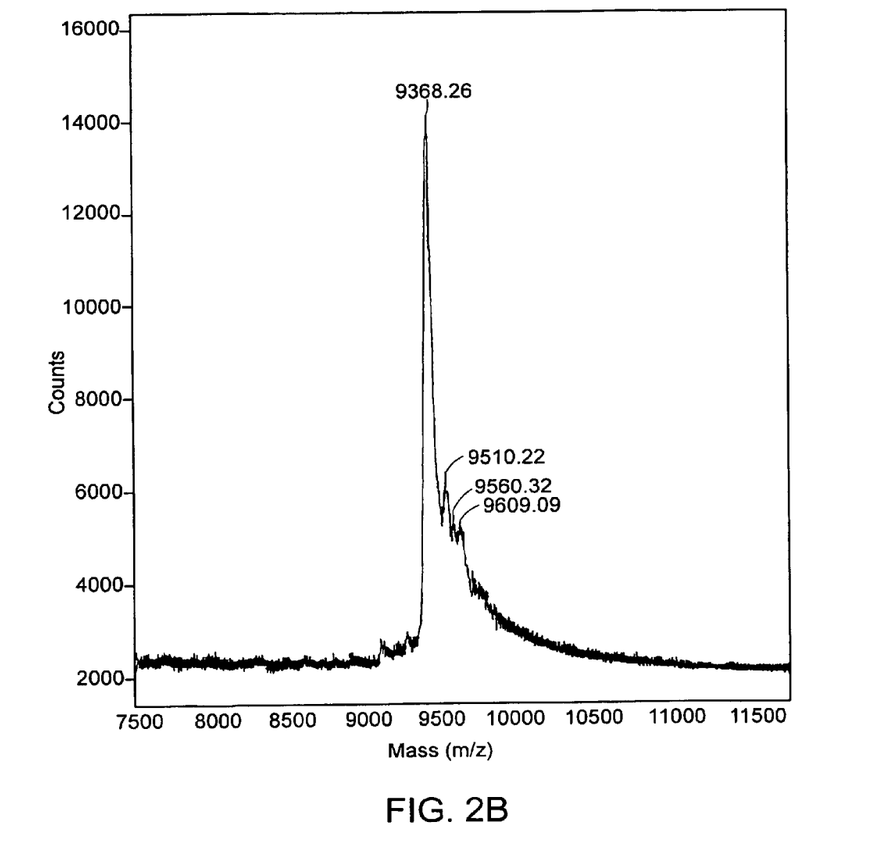
Figure 2C:
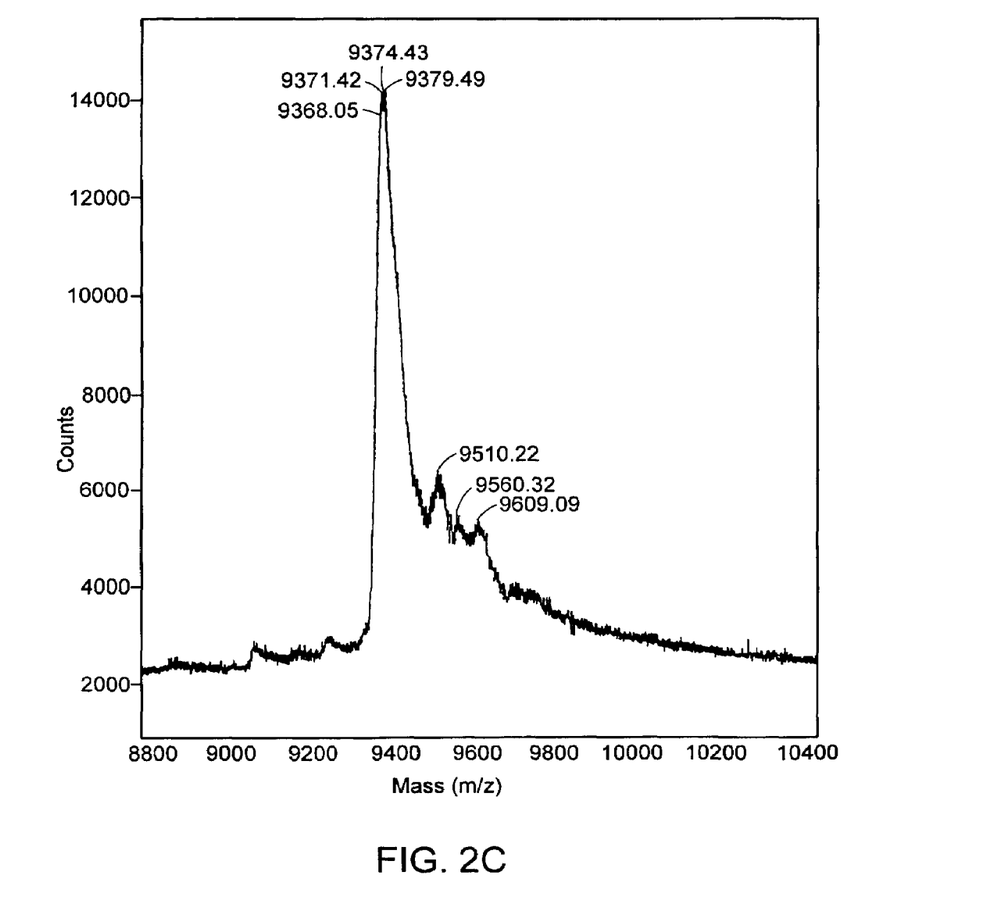

A phosphate diester oligonucleotide and a phosphorothioate oligonucleotide which each had 31 thymidine bases were synthesized in two separate batches on a rigid polystyrene solid support on DNA synthesizer 8909 Expedite (Applied Biosystems) following a standard protocol for phosporamidite chemistry. The 5'-dimethoxytrityl protecting group was left on at the end of the synthesis cycle. At the end of chain elongation, solid supports with fully protected phosphate diester or phosphorothioate oligonucleotide were divided into three parts. Each part was separately treated at 50° C. for 16 hrs. with (i) concentrated ammonium hydroxide, (ii) 10% (vol/vol) t-butylamine in concentrated ammonium hydroxide, or (iii) 5% (vol/vol) DTT in concentrated ammonium hydroxide. These samples were analyzed by ion exchange HPLC and by MALDITOF mass spectrometry (see FIGS. 1A–1C and 2A–2C for results obtained with the phosphate diester oligonucleotide). In both the phosphate diester and the phosphorothioate samples, the HPLC chromatograms showed that the portion of the sample treated with ammonium hydroxide showed the presence of an additional peak after, and close to, the product peak. In the other two portions of the sample that were treated with ammonium hydroxide and acrylonitrile scavenger, the additional peak was negligible.

The MALDITOF mass spectra (see FIG. 2A) of the 31mer polythymidine phosphate diester, which was cleaved from the solid support with concentrated ammonium hydroxide, showed a peak at 9368.32 which represents the desired product. In addition, the peaks at 9390.56 and 9409.46 represent the sodium salt and the potassium salt, respectively, of the desired product. There is a significant amount of the cyanoethylated phosphate diester which has a mass of 9423.08. In contrast, in the 3mer polythymidine phosphate diester which was cleaved from the solid support with ammonium hydroxide and 10% (vol/vol) t-butylamine (FIG. 2B) or ammonium hydroxide and 5% (vol/vol) DTT (FIG. 2C), the peak at 9423.08, which represents the cyanoethylated phosphate diester is absent.

Example 2

Two Step Deprotection Method

A phosphate diester oligonucleotide and a phosphorothioate oligonucleotide which each had 31 thymidine bases were synthesized in two separate batches on a rigid polystyrene solid support on DNA synthesizer 8909 Expedite (Applied Biosystems) following a standard protocol for phosporamidite chemistry. The 5'-dimethoxytrityl protecting group was left on at the end of the synthesis cycle. At the end of chain elongation, solid supports with fully protected phosphate diester or phosphorothioate oligonucleotide were treated with an acetonitrile solution containing 15% t-butylamine for 45 min. The support bound phosphate diester or phosphorothioate oligonucleotide was then separately treated at 50° C. for 16 hrs. with 10% (vol/vol) t-butylamine in concentrated ammonium hydroxide. These samples were analyzed by ion exchange HPLC and by MALDITOF mass spectrometry and gave similar results as those shown in FIGS. 1B and 2B for the phosphate diester oligonucleotide.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of substantially preventing modification of a synthetic oligonucleotide or oligonucleotide analog during removal of at least one β-cyanoethyl protecting group from the oligonucleotide or oligonucleotide analog, comprising the step of contacting a β-cyanoethyl protected oligonucleotide or oligonucleotide analog with an aqueous basic solution under conditions sufficient to remove at least one β-cyanoethyl protecting group, wherein the aqueous basic solution comprises at least one substituted or unsubstituted sterically hindered primary aliphatic amine.

2. The method of claim 1, wherein the β-cyanoethyl protecting groups are removed from a phosphate triester oligonucleotide.

3. The method of claim 1, wherein the β-cyanoethyl protecting groups are removed from a phosphorothioate oligonucleotide analog.

4. The method of claim 1, wherein the synthetic oligonucleotide or oligonucleotide analog is attached to a solid support by a covalent bond.

5. The method of claim 4, wherein the solid support is controlled-pore glass, polystyrene or poly(acrylamide).

6. The method of claim 4, wherein the oligonucleotide or oligonucleotide analog is cleaved from the solid support.

7. The method of claim 1, wherein the sterically hindered primary aliphatic amine is t-butylamine.

8. The method of claim 1, wherein the basic solution comprises an alkali metal hydroxide or an alkaline earth metal hydroxide.

9. The method of claim 1, wherein the basic solution is an ammonium hydroxide solution.

10. The method of claim 9, wherein the temperature of the ammonium hydroxide solution is about 20° C. to about 100° C.

11. The method of claim 10, wherein the temperature of the ammonium hydroxide solution is about 20° C. to about 35° C.

12. The method of claim 11, wherein the temperature of the ammonium hydroxide solution is about 25° C.

13. The method of claim 9, wherein the synthetic oligonucleotide or oligonucleotide analog is contacted with the ammonium hydroxide solution for about 0.5 hours to about 48 hours.

14. The method of claim 13, wherein the synthetic oligonucleotide or oligonucleotide analog is contacted with the ammonium hydroxide solution for about 0.5 hours to about 2 hours.

15. The method of claim 1, wherein the combined percentage of nucleobases which are thymine and guanine in the oligonucleotide or oligonucleotide analog is at least about 5%.

16. The method of claim 15, wherein the combined percentage of nucleobases which are thymine and guanine in the oligonucleotide or oligonucleotide analog is at least about 25%.

17. The method of claim 16, wherein the combined percentage of nucleobases which are thymine and guanine in the oligonucleotide or oligonucleotide analog is at least about 50%.

18. The method of claim 17, wherein all the nucleobases are thymine or guanine.

19. A method of substantially preventing modification of a synthetic oligonucleotide or oligonucleotide analog during removal of at least one β-cyanoethyl protecting group and at least one nucleobase protecting group from the oligonucleotide or oligonucleotide analog, comprising the step of contacting a β-cyanoethyl protected oligonucleotide or oligonucleotide analog with an aqueous basic solution under conditions sufficient to remove at least one β-cyanoethyl protecting group and at least one nucleobase protecting group, wherein the aqueous basic solution comprises at least one substituted or unsubstituted sterically hindered primary aliphatic amine.

20. The method of claim 19, wherein the β-cyanoethyl protecting groups and the nucleobase protecting groups are removed from a phosphate diester oligonucleotide.

21. The method of claim 19, wherein the β-cyanoethyl protecting groups and the nucleobase protecting groups are removed from a phosphorothioate oligonucleotide analog.

22. The method of claim 19, wherein the synthetic oligonucleotide or oligonucleotide analog is attached to a solid support by a covalent bond.

23. The method of claim 22, wherein the solid support is controlled-pore glass, polystyrene or poly(acrylamide).

24. The method of claim 22, wherein the oligonucleotide or oligonucleotide analog is cleaved from the solid support.

25. The method of claims 19, wherein the sterically hindered primary aliphatic amine is t-butylamine.

26. The method of claim 19, wherein the basic solution comprises an alkali metal hydroxide or an alkaline earth metal hydroxide.

27. The method of claim 19, wherein the basic solution is an ammonium hydroxide solution.

28. The method of claim 27, wherein the temperature of the ammonium hydroxide solution is about 20° C. to about 100° C.

29. The method of claim 28, wherein the temperature of the ammonium hydroxide solution is about 45° C. to about 65° C.

30. The method of claim 29, wherein the temperature of the ammonium hydroxide solution is about 55° C.

31. The method of claim 27, wherein the synthetic oligonucleotide or oligonucleotide analog is contacted with the ammonium hydroxide solution for about 0.5 hours to about 48 hours.

32. The method of claim 31, wherein the synthetic oligonucleotide or oligonucleotide analog is contacted with the ammonium hydroxide solution for about 6 hours to about 16hours.

33. The method of claim 19, wherein the combined percentage of nucleobases which are thymine and guanine in the oligonucleotide or oligonucleotide analog is at least about 5%.

34. The method of claim 33, wherein the combined percentage of nucleobases which are thymine and guanine in the oligonucleotide or oligonucleotide analog is at least about 25%.

35. The method of claim 34, wherein the combined percentage of nucleobases which are thymine and guanine in the oligonucleotide or oligonucleotide analog is at least about 50%.

36. The method of claim 35, wherein all the nucleobases are thymine or guanine.

37. A method of substantially preventing modification of a synthetic oligonucleotide or oligonucleotide analog during removal of at least one β-cyanoethyl protecting group and at least one nucleobase protecting group from the oligonucleotide or an oligonucleotide analog, comprising the step of contacting a β-cyanoethyl protected oligonucleotide or oligonucleotide analog with an ammonium hydroxide solution, wherein the solution contains t-butylamine, and wherein the contact is under conditions sufficient to remove at least one nucleobase protecting group and at least one β-cyanoethyl protecting group.

38. The method of claim 37, wherein a the β-cyanoethyl protecting groups and the nucleobase protecting groups are removed from a phosphate triester oligonucleotide.

39. The method of claim 37, wherein a the β-cyanoethyl protecting groups and the nucleobase protecting groups are removed from a phosphorothioate oligonucleotide analog.

40. The method of claim 37, wherein the synthetic oligonucleotide or oligonucleotide analog is attached to a solid support by a covalent bond.

41. The method of claim 40, wherein the solid support is controlled-pore glass, polystyrene or poly(acrylamide).

42. The method of claim 40, wherein the oligonucleotide or oligonucleotide analog is cleaved from the solid support.

43. The method of claim 37, wherein the temperature of the ammonium hydroxide solution is about 20° C. to about 100° C.

44. The method of claim 43, wherein the temperature of the ammonium hydroxide solution is about 45° C. to about 65° C.

45. The method of claim 44, wherein the temperature of the ammonium hydroxide solution is about 55° C.

46. The method of claim 37, wherein the synthetic oligonucleotide or oligonucleotide analog is contacted with the ammonium hydroxide solution for about 0.5 hours to about 48 hours.

47. The method of claim 46, wherein the synthetic oligonucleotide or oligonucleotide analog is contacted with the ammonium hydroxide solution for about 6 hours to about 16 hours.

48. The method of claim 37, wherein the combined percentage of nucleobases which are thymine and guanine in the oligonucleotide or oligonucleotide analog is at least about 5%.

49. The method of claim 48, wherein the combined percentage of nucleobases which are thymine and guanine in the oligonucleotide or oligonucleotide analog is at least about 25%.

50. The method of claim 49, wherein the combined percentage of nucleobases which are thymine and guanine in the oligonucleotide or oligonucleotide analog is at least about 50%.

51. The method of claim 50, wherein all the nucleobases are thymine or guanine.

52. A method of producing an oligonucleotide or oligonucleotide analog, wherein modification of the oligonucleotide or oligonucleotide analog during removal of at least one β-cyanoethyl protecting group is substantially prevented, comprising the steps of:
a) synthesizing an oligonucleotide or oligonucleotide analog having at least one β-cyanoethyl protecting group; and
b) contacting the β-cyanoethyl protected oligonucleotide or oligonucleotide analog with an aqueous basic solution, wherein the solution comprises at least one substituted or unsubstituted sterically hindered primary aliphatic amine, and wherein the contact is under conditions sufficient to remove at least one β-cyanoethyl protecting group, whereby the β-cyanoethyl protecting group is removed without substantially modifying the oligonucleotide or oligonucleotide analog.

53. The method of claim 52, wherein the synthetic oligonucleotide or oligonucleotide analog is synthesized using phosphoramidite chemistry.

54. The method of claim 53, wherein at least one nucleobase protecting group is cleaved when the synthetic oligonucleotide or oligonucleotide analog is contacted with the aqueous basic solution.

55. The method of claim 52, wherein the oligonucleotide produced is a phosphate diester oligonucleotide.

56. The method of claim 52, wherein a the oligonucleotide analog produced is a phosphorothioate oligonucleotide analog.

57. The method of claim 52, wherein the synthetic oligonucleotide or oligonucleotide analog is attached to a solid support by a covalent bond.

58. The method of claim 57, wherein the solid support is controlled-pore glass, polystyrene or poly(acrylamide).

59. The method of claim 57, wherein the oligonucleotide or oligonucleotide analog is cleaved from the solid support.

60. The method of claim 52, wherein the sterically hindered primary aliphatic amine is t-butylamine.

61. The method of claim 52, wherein the basic solution comprises an alkali metal hydroxide or an alkaline earth metal hydroxide.

62. The method of claim 52, wherein the basic solution is an ammonium hydroxide solution.

63. The meted of claim 62, wherein the temperature of the ammonium hydroxide solution is about 20° C. to about 100° C.

64. The method of claim 63, wherein the temperature of the ammonium hydroxide solution is about 20° C. to about 35° C.

65. The method of claim 64, wherein the temperature of the ammonium hydroxide solution is about 25° C.

66. The method of claim 62, wherein the synthetic oligonucleotide or oligonucleotide analog is contacted with the ammonium hydroxide solution for about 0.5 hours to about 48 hours.

67. The method of claim 66, wherein the synthetic oligonucleotide or oligonucleotide analog is contacted with the ammonium hydroxide solution for about 0.5 hours to about 2 hours.

68. The method of claim 54, wherein the basic solution is an ammonium hydroxide solution.

69. The method of claim 68, wherein the temperature of the ammonium hydroxide solution is about 20° C. to about 100° C.

70. The method of claim 69, wherein the temperature of the ammonium hydroxide solution is about 45° C. to about 65° C.

71. The method of claim 70, wherein the temperature of the ammonium hydroxide solution is about 55° C.

72. The method of claim 68, wherein the synthetic oligonucleotide or oligonucleotide analog is contacted with the ammonium hydroxide solution for about 0.5 hours to about 48 hours.

73. The method of claim 72, wherein the synthetic oligonucleotide or oligonucleotide analog is contacted with the ammonium hydroxide solution for about 6 hours to about 16 hours.

74. The method of claim 54, wherein the combined percentage of nucleobases which are thymine and guanine in the oligonucleotide or oligonucleotide analog is at least about 5%.

75. The method of claim 73, wherein the combined percentage of nucleobases which are thymine and guanine in the oligonucleotide or oligonucleotide analog is at least about 25%.

76. The method of claim 75, wherein the combined percentage of nucleobases which are thymidine and guanine in the oligonucleotide or oligonucleotide analog is at least about 50%.

77. The method of claim 76, wherein all the nucleobases are thymine or guanine.

78. A method of preparing an oligonucleotide or oligonucleotide analog comprising removing at least one β-cyanoethyl group from a β-cyanoethyl protected oligonucleotide or oligonucleotide analog using the method of any one preceding claim.

* * * * *